United States Patent [19]

Oberlin et al.

[11] Patent Number: 5,562,682
[45] Date of Patent: Oct. 8, 1996

[54] SURGICAL INSTRUMENT WITH ADJUSTABLE ARMS

[75] Inventors: Jeffrey R. Oberlin; Randall J. Hoyt, both of Kalamazoo, Mich.

[73] Assignee: Richard-Allan Medical Industries, Inc., Richland, Mich.

[21] Appl. No.: 134,522

[22] Filed: Oct. 8, 1993

[51] Int. Cl.$^6$ .................................... A61B 17/00
[52] U.S. Cl. ........................ 606/139; 606/143; 227/901; 227/175.1
[58] Field of Search .................. 606/139, 142, 606/143, 144, 148, 205, 206–208; 227/175–182, 901, 19

[56] References Cited

U.S. PATENT DOCUMENTS

| | | | |
|---|---|---|---|
| Re. 28,932 | 8/1976 | Noiles et al. | 227/19 |
| D. 327,323 | 6/1992 | Hunt | D24/145 |
| 3,314,431 | 4/1967 | Smith, Jr. | 128/351 |
| 3,837,555 | 9/1974 | Green | 227/130 |
| 4,185,762 | 1/1980 | Froehlich | 227/138 |
| 4,196,836 | 4/1980 | Becht | 227/110 |
| 4,471,781 | 9/1984 | De Giovanni et al. | 128/334 R |
| 4,473,077 | 9/1984 | Noiles et al. | 128/305 |
| 4,485,817 | 12/1984 | Swiggett | 128/334 R |
| 4,488,523 | 12/1984 | Shichman | 128/334 R |
| 4,566,620 | 1/1986 | Green et al. | 227/19 |
| 4,573,622 | 3/1986 | Green et al. | 227/19 |
| 4,606,343 | 8/1986 | Conta et al. | 128/305 |
| 4,610,383 | 9/1986 | Rothfuss et al. | 227/19 |

(List continued on next page.)

FOREIGN PATENT DOCUMENTS

| | | |
|---|---|---|
| 0167217 | 2/1985 | European Pat. Off. ........ A61B 17/10 |
| 0324638 | 1/1989 | European Pat. Off. ........ A61B 17/10 |
| 0324637 | 1/1989 | European Pat. Off. ........ A61B 17/10 |
| 0324636 | 1/1989 | European Pat. Off. ........ A61B 17/10 |
| 0324635 | 1/1989 | European Pat. Off. ........ A61B 17/10 |
| 0484671 | 9/1991 | European Pat. Off. ........ A61B 17/32 |
| 0557806 | 8/1932 | Germany. |
| 0567146 | 12/1932 | Germany. |
| 0582295 | 8/1933 | Germany. |
| 0592244 | 3/1934 | Germany. |
| 0593920 | 3/1934 | Germany. |
| 0598529 | 6/1934 | Germany. |
| 869388 | 6/1953 | Germany. |
| PCT/US92/08325 | 9/1992 | WIPO ............. A61B 17/28 |
| WO93/07816 | 4/1993 | WIPO ................. 606/205 |

OTHER PUBLICATIONS

Advertisement for Appose Ultra Stapler, Davis & Geck, 1989.
Advertisement for Auto Suture Company Products, 1992.
Advertisement for Endo Universal 65 Stapler, Auto Suture, 1993.
Advertisement for Endopath Surgical Instrument, Ethicon (in German).
Advertisement for Endopath Articulating Surgical Instrument, Ethicon, 1992.
Advertisement for Auto Suture Multifire Premium Skin Stapler, 1990.
Advertisement for Proximate RH Rotating Head Skin Stapler, Ethicon.
Advertisement for Weck 360 LX Rotating Head Skin Stapler.
Advertisement for AutoSuture Endo Hernia Instrument (in German).

*Primary Examiner*—Gary Jackson
*Assistant Examiner*—Jeffrey A. Schmidt

[57] ABSTRACT

A surgical instrument for endoscopic surgery is provided which is capable of articulation in the endoscopic arm portion of the instrument to supply the surgeon with improved adjustability in the orientation of the arm. The instrument provides means through which the surgeon can change the angle at which the instrument actuates. This articulation functions without disruption of the rotatability of the arm or the mechanism for applying staples, clips, and the like. Because this articulation can be performed in conjunction with a rotation feature, a large degree of adjustment is generated.

60 Claims, 6 Drawing Sheets

U.S. PATENT DOCUMENTS

| | | | |
|---|---|---|---|
| 4,674,501 | 6/1987 | Greenberg | 128/305 |
| 4,691,853 | 9/1987 | Storace | 227/19 |
| 4,728,020 | 3/1988 | Green et al. | 227/19 |
| 4,807,628 | 2/1989 | Peters et al. | 128/334 |
| 4,841,888 | 6/1989 | Mills et al. | 112/169 |
| 4,869,414 | 9/1989 | Green et al. | 227/19 |
| 4,872,456 | 10/1989 | Hasson | 128/321 |
| 4,880,015 | 11/1989 | Nierman | 128/751 |
| 4,951,861 | 8/1990 | Schulze et al. | 227/178 |
| 5,015,249 | 5/1991 | Nakao et al. | 606/142 |
| 5,040,715 | 8/1991 | Green et al. | 227/176 |
| 5,042,707 | 8/1991 | Taheri | 606/213 |
| 5,100,420 | 3/1992 | Green et al. | 606/143 |
| 5,161,725 | 11/1992 | Murray et al. | 227/182 |
| 5,174,487 | 12/1992 | Rothfuss et al. | 227/176 |
| 5,176,702 | 1/1993 | Bales et al. | 606/208 |
| 5,207,691 | 5/1993 | Nardella | 606/143 |
| 5,209,747 | 5/1993 | Knoepfler | 606/208 |
| 5,240,164 | 8/1993 | Murray et al. | 227/175 |
| 5,246,156 | 9/1993 | Rothfuss et al. | 227/176 |
| 5,271,543 | 12/1991 | Grant et al. | 227/179 |
| 5,289,963 | 3/1994 | McGarry et al. | 227/182 |
| 5,312,023 | 5/1994 | Green et al. | 227/19 |
| 5,312,024 | 5/1994 | Grant et al. | 227/179 |
| 5,314,424 | 5/1994 | Nicholas | 606/41 |
| 5,320,637 | 6/1994 | Borders, Jr. | 606/207 |
| 5,326,013 | 7/1994 | Green et al. | 227/176 |
| 5,330,502 | 7/1994 | Hassler et al. | 606/170 |
| 5,346,504 | 9/1994 | Ortiz et al. | 606/192 |
| 5,356,064 | 10/1994 | Green et al. | 227/177 |
| 5,364,002 | 11/1994 | Green et al. | 227/177 |
| 5,374,277 | 12/1994 | Hassler | 606/207 |
| 5,381,943 | 1/1995 | Allen et al. | 227/177 |
| 5,392,978 | 2/1995 | Velez et al. | 227/177 |
| 5,409,498 | 4/1995 | Braddock et al. | 606/143 |
| 5,413,272 | 5/1995 | Green et al. | 227/175 |

SURGICAL INSTRUMENT WITH ADJUSTABLE ARMS

FIELD OF THE INVENTION

The present invention relates generally to surgical instruments and more specifically concerns endoscopic surgical instruments with articulation and rotation adjustment features to facilitate accurate application of staples, clips and the like.

BACKGROUND OF THE INVENTION

In surgical procedures, the surgeon generally requires instruments capable of actuating in precise locations and directions. The surgical stapling apparatus and the clip applier are two examples of such instruments. Endoscopic surgical use of those instruments, in particular, poses special problems.

In laparoscopic surgery, after a patient's abdominal cavity is filled with gas, a trocar is utilized to puncture the skin of the patient's body cavity. When the obuator of the trocar is removed, a cylindrical tube or cannula from the trocar is positioned within the skin. This tube or cannula provides an opening through which the surgeon can access the inner body of the patient. The surgeon performs the surgical procedure by the insertion of instruments through the tube which is inserted into the body cavity of the patient.

These instruments generally possess long arms or shafts which pass through the tube. An actuation mechanism is located at the distal end of the arm or shaft which is inserted through the tube. A handle with the operating controls is located at the other end or proximal end of the arm, which is exposed externally during surgery. Thus, the surgeon can externally control the functions of the instrument.

However, because the walls of the tube rigidly constrain the angle at which the arm of the surgical instrument can be inserted and because the tube has restricted orientation with respect to the body cavity, the surgeon is afforded little adjustability in the location and angle of the actuation mechanism of the inserted surgical instrument. For the most part, the instrument is held in a parallel position relative to the trocar tube. Thus, a surgeon operating within the body cavity of a patient is restricted in the orientation of the surgical instruments used within the body cavity. In other words, the surgical instrument can be inserted into the patient's body at a limited angular range.

This limitation in adjustability conflicts with the requirements of the surgical procedure. For example, some of the body tissue to be operated on may lie in places difficult to reach or at angles which are difficult to accommodate. Furthermore, in any single procedure, the body tissue to be operated on will lie in various positions and angles.

Accordingly, the surgeon needs to be able to adjust the location and angle of the surgical instrument in order to accurately manipulate or fasten body tissue. Without any ability to adjust the orientation of the actuation mechanism, an entirely new trocar tube would have to be inserted into the patient's body at another location. Clearly, the insertion of additional trocar tubes is to be avoided.

For these reasons, it is desirable for a surgical instrument to have flexible movement in the area of the clip-applying, stapling or other actuation mechanism. However, designing an inexpensive and reliable articulation and rotational feature has many considerations.

By necessity, the actuation mechanism must be located at the distal part of the endoscopic arm while the controls must be located at the end of the instrument externally exposed during surgery so that the surgeon can access them. The drive rod and cable assembly which transmits the linear force runs the length of the instrument from the controls end to the actuation mechanism. To provide optimal flexibility, the articulation feature must operate at the end of the instrument within the body cavity near the actuation mechanism. Consequently, the linear force must be transmitted through the bent drive cable without creating a moment force. A moment would cause unwanted cartridge articulation; it might also make it difficult for the surgeon to maintain steady positioning of the instrument.

Further, this drive cable must be capable of repeated bending and straightening. To ensure reliability, a material capable of withstanding this repeated cycle must be utilized. In addition, the compressive and tensile forces exerted on the drive cable should be minimized.

In addition, speed as well as accuracy is desirable during surgical procedures. Frequently, quick adjustment of the orientation of the surgical instrument is critical. Furthermore, articulation should not require the exertion of additional pressure by the surgeon to trigger the instrument. The trigger pressure should remain as low as possible without risking accidental triggering.

Articulation of the arm of the surgical instrument provides significant adjustability to the actuation direction. This adjustability is immensely enhanced when used in conjunction with a rotation feature. Consequently, the articulation feature must accommodate a rotational feature. Furthermore, increased stability in the position of rotation adjustment is generally desirable. While a certain lack of stability in the rotational positioning of the arm of the surgical instrument could be tolerated if the instrument has no articulation feature, the presence of an articulation feature increases the need for stability in rotational positioning.

The surgeon only has two hands and one of his hands is needed to pull the trigger to actuate the mechanism. Consequently, the surgeon must rely upon the arm remaining at one rotation position so that the articulation feature can be adjusted accordingly. This situation is true in the reverse and is especially true if a number of iterations in adjustment is necessary. Thus, a means of stability for the rotational positioning feature and the articulation feature are essential aspects of a surgical instrument.

SUMMARY OF THE INVENTION

It is the primary aim of the present invention to provide an articulation feature for a surgical instrument such that the user of the instrument can adjust the direction of actuation of the instrument within a patient's body cavity. Furthermore, it is an object to accomplish maximum angular range of the articulation of the arm.

Another object is to provide stability to the orientation chosen by the surgeon. Stability in both the angular position and the rotated position is important. It is a further object of the invention to provide articulation and rotation features to the surgical instrument in a manner whereby both features can operate simultaneously.

Providing ease and rapidity in adjustment and use of the surgical instrument are other important objectives of this invention. Consequently, it is also an object of this invention to minimize the force the surgeon must use to articulate or rotate the arm of the instrument. The minimization of the level of pressure required to trigger the instrument is a related object of the invention. It is desired that the trigger pressure be minimized regardless of the degree of articulation or rotation at which the instrument is placed. It is further an object of this invention to prevent moment changes creating unwanted cartridge articulation.

Another object of this invention is to provide reliability, particularly under conditions of frequent use. Accordingly, reduction in cable stresses and compression is also an object of this invention.

Accordingly, the subject invention provides for improved articulation mechanisms and surgical instruments utilizing such improved mechanisms. In general, the surgical instruments have a proximal arm and a distal arm which are connected by an articulation mechanism. The articulation mechanism comprises a pivot gear which is located on one of the arms. The pivot gear engages a pivot rack which is located on the other arm.

As will become apparent from the detailed description below, the improved articulation mechanism provides a high degree of articulation in a simple and efficient manner. The mechanism also helps to eliminate movements and to reduce stress in flexible drive members passing therethrough.

In other aspects, the subject invention provides for improved force transmission mechanisms and surgical instruments utilizing such improved mechanisms. In general, the surgical instruments have a proximal arm and a distal arm which are pivotally connected for articulation. A force transmission mechanism passes through the articulation joint. The force transmission mechanism comprises a flexible drive member and a backstop. The backstop is pivotally connected to one of the arms and is slidably connected to the other arm.

Such force transmission mechanisms accommodate articulation of the arms yet require relatively low actuation forces, even when the instrument is articulated. Further, the improved mechanisms offer relatively little resistance to articulation. The backstop also helps to eliminate moments and to reduce stress in the flexible drive member.

Other aspects of the subject invention provide for improved arm rotation mechanisms and surgical instruments utilizing the improved rotation mechanisms. The surgical instruments in general have a rotatable arm which is connected to a handle. A protrusion is located between the handle and the arm, and a U-shaped, resilient metal wire member is located between the arm and the protrusion. The resilient member successively engages a plurality of grooves in the protrusion as the arm is rotated. Thus, the arm may be adjusted and held in a plurality of fixed rotational positions.

Such rotation mechanisms, as will be apparent from the detailed description which follows, allow the arm to be adjusted and held in discrete rotational positions in a relatively simple and efficient manner. The force required to move the arm from one rotational position to the next also may be adjusted easily.

Moreover, the novel mechanisms, because they have a relatively simple design utilizing relatively few parts, enable a wide variety of other mechanisms having different configuration or functions to be incorporated into the instrument. Thus, the subject invention also provides for instruments having more than one of the aforementioned novel mechanisms and which may have a variety of other mechanisms.

Other objects and advantages of the present invention and its details of construction will be apparent from a consideration of the following specification and accompanying drawings.

While the invention will be described in connection with certain preferred embodiments, it is not intended to limit the invention to those embodiments. On the contrary, it is intended to cover all alternatives, modifications and equivalents as may be included within the spirit and scope of the invention.

DETAILED DESCRIPTION OF THE PREFERRED EMBODIMENT

Figure 1:
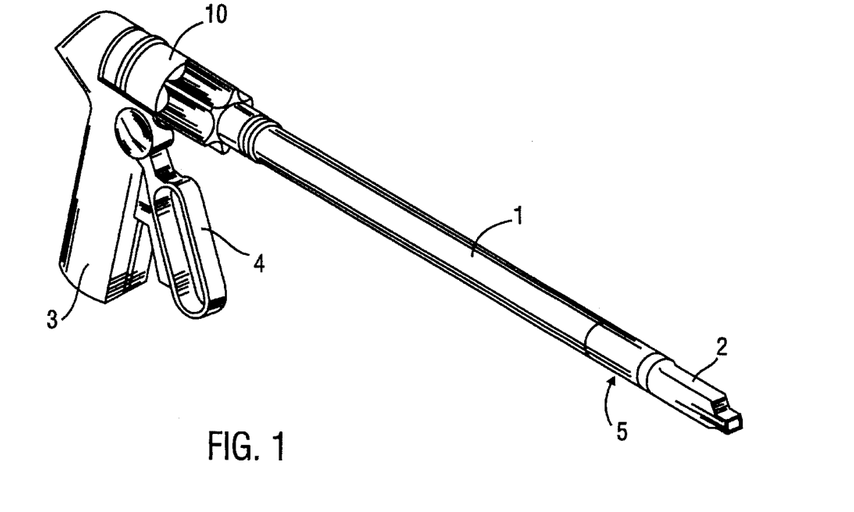
FIG. 1 is a right front perspective view of the surgical instrument.
Figures 2, 3, 4:
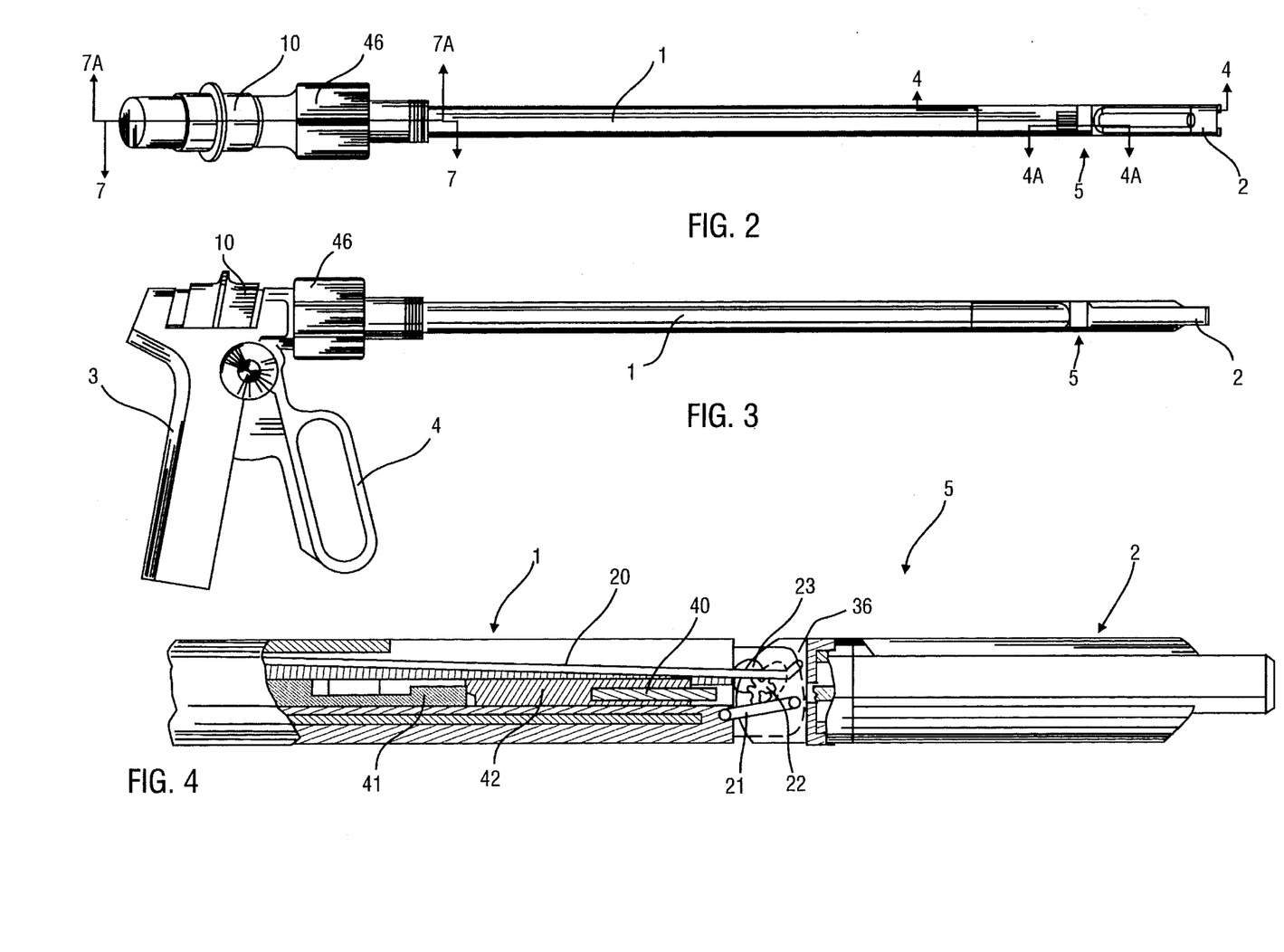
FIG. 2 is top plan view of the surgical instrument.
FIG. 3 is right side elevational view of the surgical instrument.
FIG. 4 is a partial cross-sectional view taken along line 4—4 of FIG. 2 showing the articulation feature at 0 degrees of articulation.
Figure 4A:
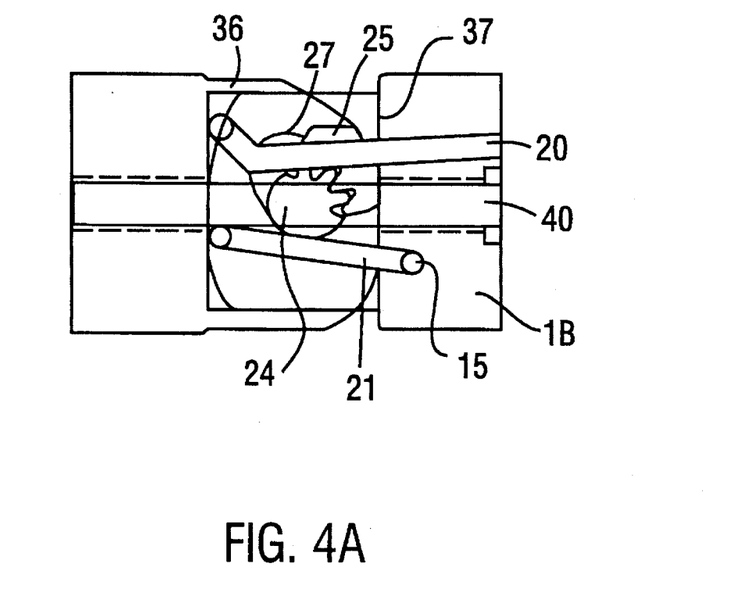
FIG. 4A is an enlarged partial cross-sectional view taken along line 4A—4A of FIG. 2 showing the articulation feature at 0 degrees or articulation.

Turning now to the drawings, FIGS. 1, 2 and 3 show one embodiment of the surgical instrument in perspective, top and front views, respectively. Generally speaking, a surgical instrument, particularly those used in endoscopic surgery, includes a long endoscopic arm portion 1, an actuation mechanism 2 located at the end of the endoscopic arm portion 1 and a handle area 3 with a trigger 4. The operation of the trigger 4 causes a linear force to travel through the length of the arm 1 to the actuation mechanism 2. This linear force activates the actuation mechanism 2. The actuation mechanism 2 can include, but is not limited to, staplers, clip appliers, scissors, linear staplers, GIA stapling and dividing devices, graspers, or other such instruments.

Figure 5:
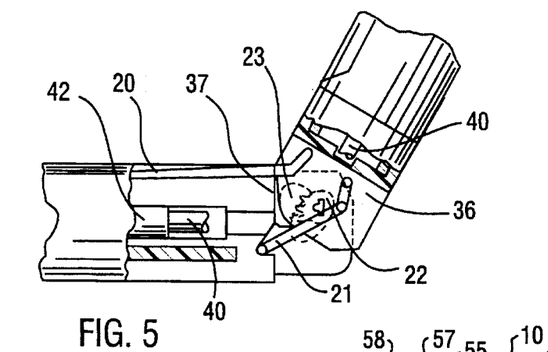
FIG. 5 is a partial cross-sectional view taken along line 4—4 of FIG. 2 showing the articulation feature at approximately 60 degrees of articulation.
Figure 5A:
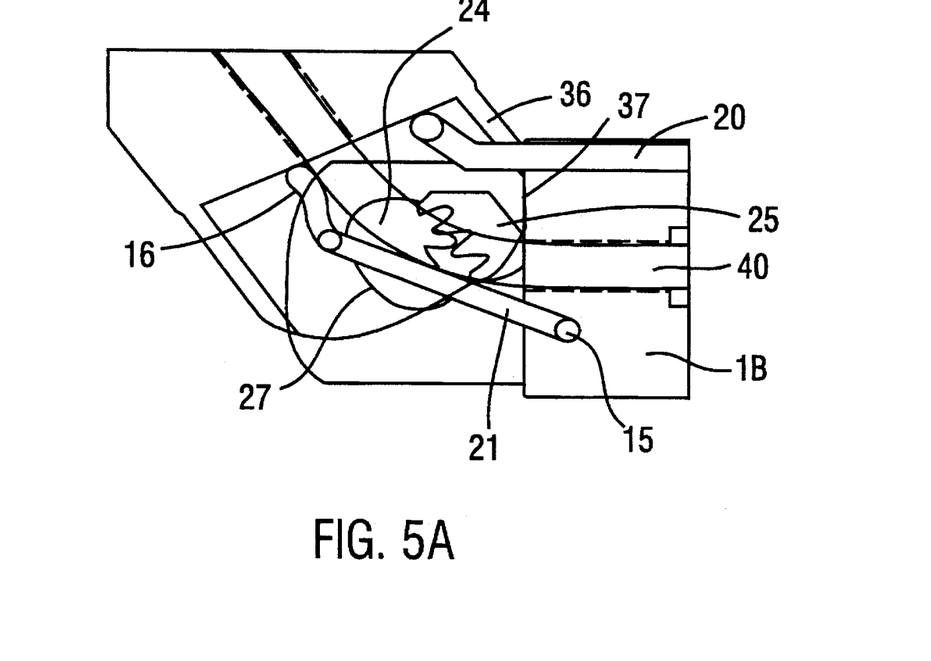
FIG. 5A is an enlarged partial cross-sectional view taken along line 4A—4A of FIG. 2 showing the articulation feature at approximately 60 degrees of articulation.
Figure 6:
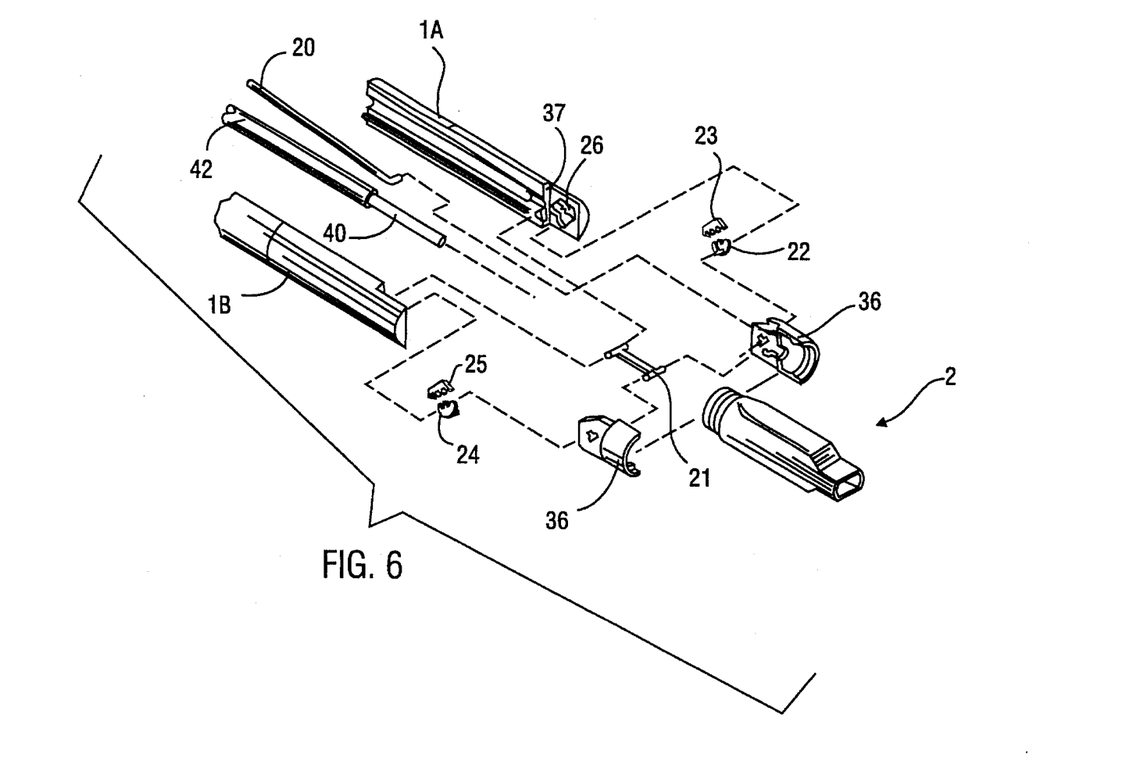
FIG. 6 is a partial exploded, perspective view of the articulation feature.

As depicted in FIGS. 4–6, the invention also comprises an articulation mechanism or joint 5 which includes an articulation rod 20, a backstop 21, two pivot gears 22 and 24, and two pivot gear racks 23 and 25. Further, the actuation mechanism or cartridge 2 is connected to the endoscopic arm 1 at the joint 5. A drive cable 40 runs through the center of the joint 5 between the endoscopic arm 1 and into the cartridge 2 as shown in FIGS. 4, 4A, 5 and 5A.

The drive cable 40 consists of a flexible but strong material, such as stainless steel with a thin plastic coating. In the present embodiment of the invention, movement of the trigger 4 forces a long push rod 41 to move forward pushing a short push rod 42. The short push rod 42 is secured to the drive cable 40. The drive cable 40 will consequently move forward, regardless of any bending in the drive cable 40. The long push rod 41 and the short push rod 42 are rigid to prevent any unwanted bending. The long push rod 41 is contained within a cylindrical aperture 43 concentric to and in the center of the arm 1 which comprises arm halves 1A, 1B. The long push rod 41 is rotatably secured in a pivot bearing 45 which is located on the trigger 4.

Articulation of the invention is caused by the saddle 10 which is linked to the articulation rod 20. At zero degrees articulation, as shown in FIG. 4, the backstop 21, pivot gears 22 and 24 and pivot gear racks 23 and 25 do not perform any particular function. The drive cable 40 passes through the center of the pivot gear 22 and the centerline of the arm 1.

As shown in FIGS. 4, 4A, 5, 5A and 6, the racks 23 and 25 are secured within the arm halves 1A, 1B. Each rack 23, 25 is positioned within molded openings 26, 27 which have a geometry corresponding to the shape of the racks. The gears 22, 24 are attached to each half of the knuckle 36 by inserting a T-shaped or other shaped protrusion on the gears 22, 24 into a T-shaped or correspondingly shaped opening in each half of the knuckle 36. The molded openings 26, 27 also have an area corresponding to the gears 22 and 24, but the gears 22 and 24 are allowed to rotate up the teeth of the racks 23 and 25.

At an articulated angle, however, the functioning of these pieces is critical to this invention. The operation occurs when the saddle 10 is moved laterally. The articulation rod 20 is operably attached to the saddle 10 at one end and rotatably attached at opening 35 in the knuckle 36 of the cartridge 2. When the saddle 10 is moved laterally, the articulation rod 20, which travels the length of the arm 1, causes the cartridge 2 to move angularly relative to the arm 1 as shown in FIGS. 5 and 5A.

This angular movement of the cartridge 2 is achieved because the lateral movement of the articulation rod 20 pulls the cartridge 2 toward the arm 1. The cartridge 2 begins to articulate as the gear 22 climbs the gear rack 23. The joint 5 is predeterminately designed to provide a predictable degree of articulation depending on the position of the articulation rod 20. FIG. 5 shows the joint 5 in full articulated position.

Thus, when the trigger 4 of the instrument is squeezed, the drive cable 40 moves forward through the joint 5. The leading edge of the cable 40 is connected to a member in the actuation mechanism or cartridge 2 for accepting the linear force transmission. As the trigger force increases, the cable 40 tends to bow outward in the joint area until the outer tangent surface comes into contact with the backstop 21 as shown in FIGS. 5 and 5A. The cable 40 then resumes its forward motion. The backstop 21 has a fixed pivot point 15 in the arm 1 and follows a track 16 in the knuckle 36. This track 16 causes the backstop 21 to move in accordance with the articulation angle, thereby providing support at all angles.

The pivot gear 22 and rack 23 acts as a moment balancing joint. As the articulation angle changes, the pivot gear 22 climbs up the gear rack 23, changing the effective pivot point. The importance of this design is that the cable 40 always passes through the center of the pivot point in order to eliminate any moment that would be caused during force transmission. Another function of the pivot gear system is to eliminate cable compression above the pivot point. This compression occurs naturally with a fixed pivot point on the centerline and tends to alter the firing stroke of the trigger and also the pre-cock system.

To provide stability to the articulated position of the cartridge 2, the saddle 10 is fastened to a detent slide 55 with a protrusion 57. The protrusion 57 fits within a groove 58, which is part of a linear series. When the saddle 10 moves laterally, the detent slide 55 likewise moves. However, a detent compression spring 56, secured by ribs 59 in the handle 3, applies an upward pressure on the detent slide 55 to force the protrusion 57 to fit within one of the molded grooves 58. The spring 56 allows the saddle 10 to move when a surgeon applies a reasonable pressure to the saddle 10. Nonetheless, the spring 56 applies sufficient pressure to provide stability to the position of the saddle 10, and consequently, the articulated position of the cartridge 2.

Figure 7:
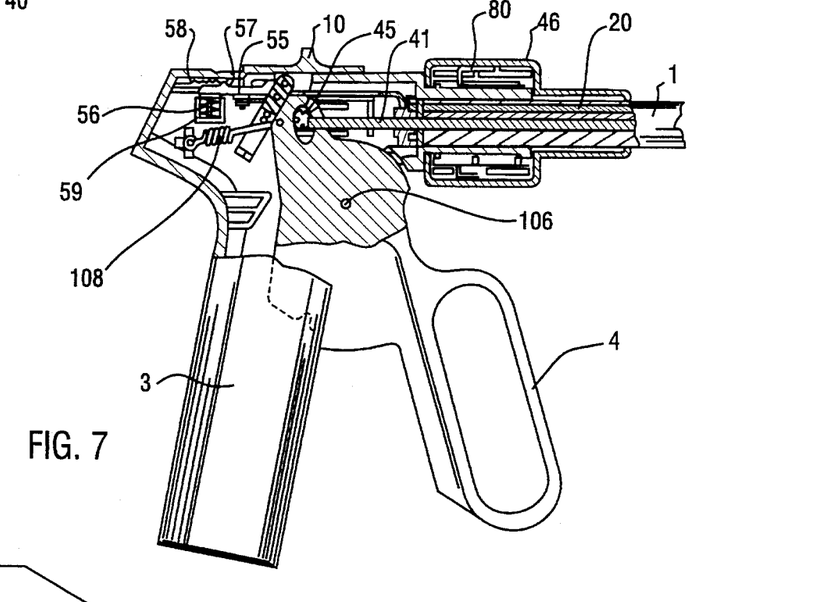
FIG. 7 is a partial cross sectional view taken along line 7—7 of FIG. 2 showing the rotation feature and handle of the surgical instrument.
Figure 7A:
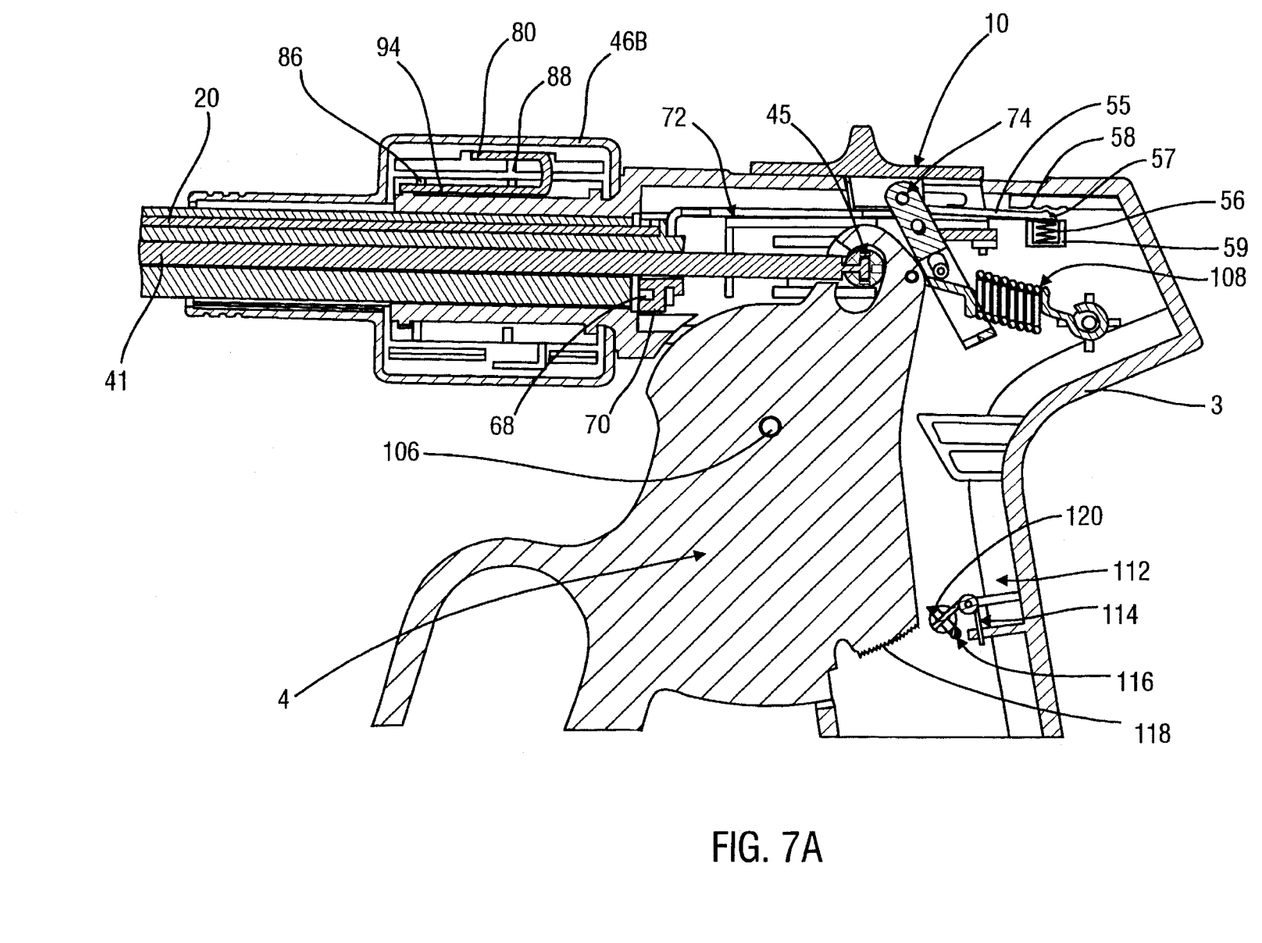
FIG. 7A is an enlarged partial cross-sectional view taken along line 7A—7A of FIG. 2.
Figure 8:
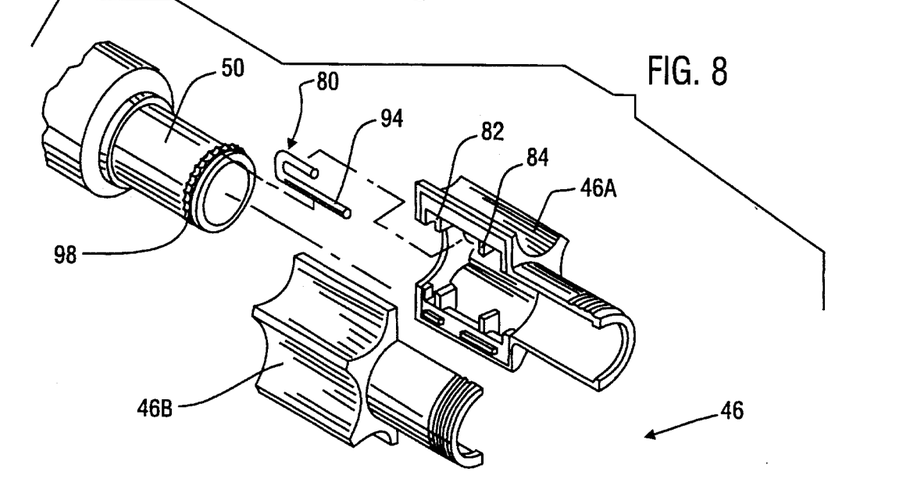
FIG. 8 is a partial perspective exploded view of the rotation feature of the surgical instrument.
Figures 9, 10, 11, 12:
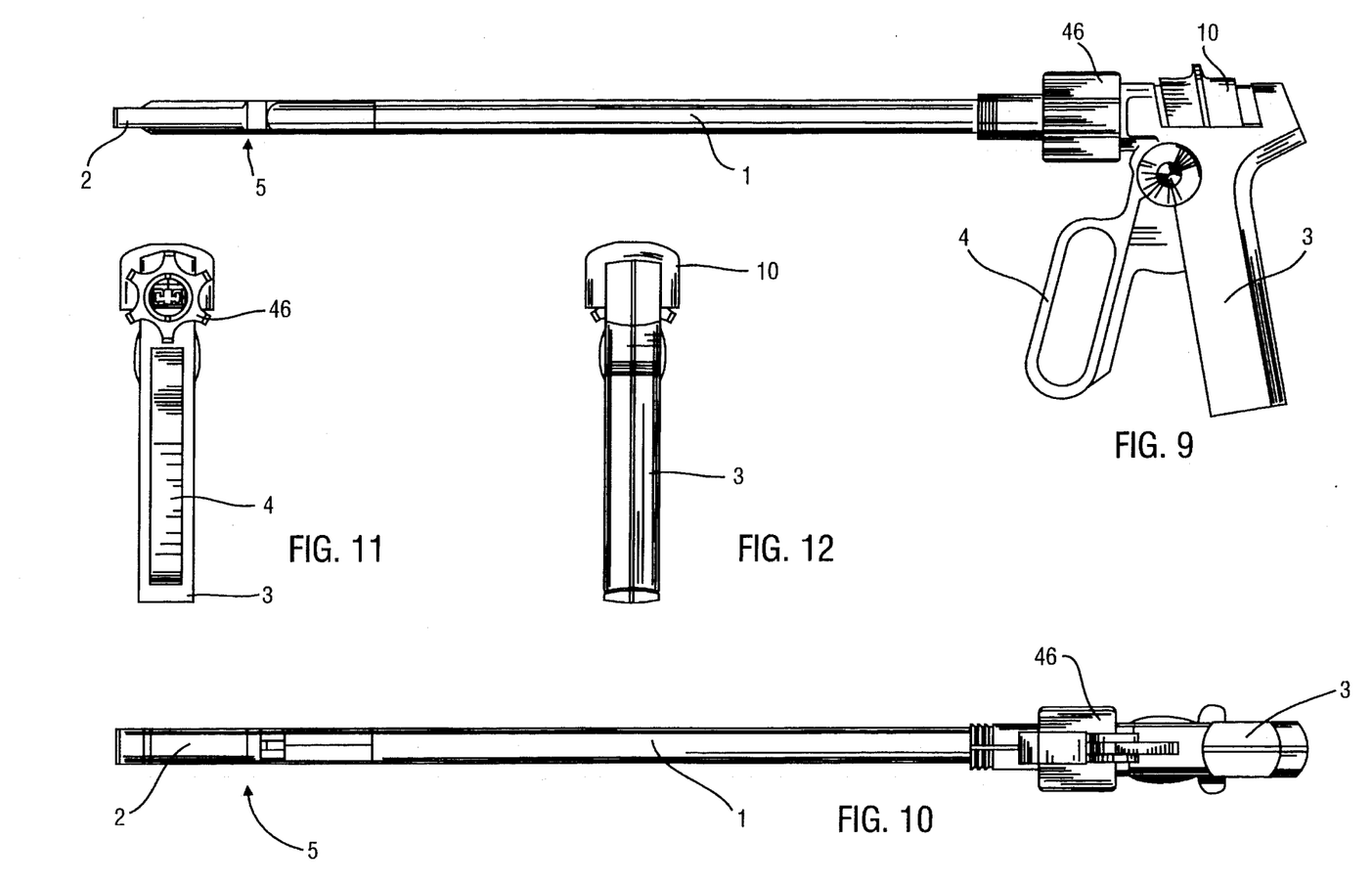
FIG. 9 is a left side elevational view of the surgical instrument.
FIG. 10 is a bottom plan view of the surgical instrument.
FIG. 11 is a front elevational view of the surgical instrument.
FIG. 12 is a rear elevational view of the surgical instrument.

FIGS. 7, 7A and 8 illustrate the rotation feature of the invention. The arm 1 is free to rotate because it is not fixedly secured to the handle 3, but is positioned within a tube-like protrusion 50 on the handle 3. The long push rod 41 travels into the handle 3 and is attached to a pivot bearing 45 in the trigger 4. The pivot housing 46 which includes housing halves 46A, 46B is fixedly attached to the arm 1 and rotatably attached to the protrusion 50. Thus, the surgeon can rotate the arm 1 without affecting the position of the handle 3 by rotating the pivot housing 46.

The articulation rod 20 maintains its relative position in the arm 1, but slides within an annular channel 68 in an articulation disk 70. The mount 72 which is operably attached to the saddle 10 by saddle linkage 74 acts on the articulation rod 20 through the articulation disk 70 regardless of the rotated position of the arm 1.

The rotation feature is provided with a detent mechanism in order to maintain the position selected by the user similar to the function of the detent mechanism for the articulation feature. Referring to FIGS. 7, 7A and 8, a resilient, U-shaped wire 80 is secured within the pivot housing 46 by two ribs 82, 84 on housing half 46A and two ribs 86, 88 on housing half 46B. As the pivot housing 46 is rotated, one leg 94 of the wire 80 deflects over the annular series of grooves 98 on the tube-like protrusion 50. Consequently, the pivot housing 46 which is ultimately connected to the actuation mechanism 2 can be held in the position selected by the user because the leg 94 will be held in one of the grooves 98 until the user selects a new position.

There are two main advantages of this detent mechanism. The first advantage is that the design minimizes the number of parts required since the U-shaped wire 80 provides both the contact surface and the spring force. The second advantage is that the detent force, i.e. the force required to rotate the device as the leg 94 deflects over one peak between the grooves 98, can easily be altered. The detent force is altered by changing the bend angle of the leg 94 in the U-shaped wire 80, without altering the annular series of grooves 98.

Referring to FIGS. 7 and 7A, the trigger 4 is attached to the handle 3 at pivot point 106. The trigger 4 is held in the open position by extension spring 108 which is attached to the trigger 4 and the handle 3. In order to move the long push rod 41 forward, the user pulls the trigger 4 rearward against the handle 3 to overcome the biasing force of the extension spring 108.

In order to ensure that the user pulls the trigger 4 through its required stroke or movement, the handle 3 includes a pre-cock system 112. Referring to FIG. 7A, the pre-cock system 112 includes pre-cock spring 114, a pre-cock latch 116 and a series of ridges 118 on the trigger 4. As the trigger 4 is pivoted rearward the ridges 118 engage the latch 116. The latch 116 deflects over each ridge 118 as the spring 114 biases the latch 116 towards the ridges 118. Due to the shape of the ridges 118 and the angular edge 120 on the latch 116, the trigger 4 can be held in a fixed position with respect to the handle 3 as the latch 116 engages each ridge 118. Consequently, the user can partially depress the trigger 4 and the pre-cock system 112 will hold the trigger 4 in the partially depressed position. Furthermore, due to the pre-cock system 112, the trigger 4 can only move in a rearward position, and cannot be moved in a forward position, until the latch 116 deflects over the last ridge 118. After the latch 116 deflects over the last ridge 118, the latch 116 achieves a different orientation and permits the trigger 4 to move forward. Thus, the pre-cock system 112 ensures that the user pulls the trigger 4 through its required stroke or movement in order to prevent double actuation of the actuation mechanism 2.

It will be appreciated, of course, that the foregoing arrangement is suitable for any instrument that requires transmission of force to an actuation mechanism 2 and requires an articulation feature. Furthermore, it will be appreciated that the foregoing invention is suitable for any instrument which requires a rotational feature which allows the user to maintain a selected rotational position.

What is claimed is:

1. A surgical instrument including an articulation mechanism comprising:
    an endoscopic arm with proximal and distal portions pivotally connected by a pivot mechanism having a pivot axis, said distal arm portion containing an actuation mechanism;
    a flexible drive cable located within said pivot mechanism and passing through said pivot axis;
    a rigid backstop element secured in the pivot mechanism, wherein said backstop supports the drive cable on said pivot axis and includes a pivot connection to one of said arm portions at one end of said backstop and a slidable connection to the other said arm portion at the other end of said backstop;
    an articulation rod located within said proximal arm portion and longitudinally moveable therein, said articulation rod being pivotally connected to said distal arm portion such that longitudinal movement of said articulation rod causes said distal arm portion to angularly move relative to said proximal arm portion.

2. The invention of claim 1 wherein said endoscopic arm is rotatably attached to a handle and operably attached to a control means for rotation.

3. The invention of claim 2 wherein said control means for rotation comprises a pivot housing containing a detent means.

4. The invention of claim 3 wherein said detent means comprises a resilient, U-shaped wire in which one leg is secured in said pivot housing and the other leg engages an annular series of grooves formed on said endoscopic arm.

5. The invention of claim 1 further comprising a rigid rod which is operatively connected with said flexible drive cable.

6. The invention of claim 1, wherein said slidable connection includes a track in the other said arm portion.

7. The invention of claim 1, wherein said pivot mechanism further comprises a pivot gear operably enjoined with a pivot gear rack.

8. The invention of claim 1, wherein said surgical instrument includes control means for causing articulation movement of said endoscopic arm, said control means operably connected to said articulation rod whereby said articulation control means causes said articulation rod to move laterally causing said distal arm portion to angularly move relative to said proximal arm portion.

9. The invention of claim 8 wherein said articulation control means comprises a saddle operatively connected to said articulation rod.

10. A mechanism for adjustably maintaining an angle of rotation of an arm with respect to a handle of a surgical device, wherein the arm is rotatably mounted to the handle, said mechanism comprising:
    a protrusion located between the handle and the arm, said protrusion having a plurality of grooves;
    a U-shaped resilient metal wire member located between the arm and said grooves, wherein said resilient member is rotatably adjustable between a plurality of fixed positions, wherein in each of said fixed positions said resilient member engages one of said grooves.

11. A mechanism according to claim 10, wherein said resilient member is connected to the arm.

12. A mechanism according to claim 11, wherein the resilient member is not integral with said arm.

13. A mechanism according to claim 11, wherein said resilient member is connected to the arm by two ribs.

14. A mechanism according to claim 13, wherein the arm includes two housing halves which contain said resilient member and said two ribs.

15. A mechanism according to claim 14, wherein the two housing halves contain four ribs.

16. A mechanism according to claim 12, wherein said protrusion is tube-like.

17. A mechanism according to claim 16, wherein said protrusion extends from the handle.

18. A mechanism according to claim 17, wherein said grooves comprise an annular series of grooves.

19. A mechanism according to claim 18, wherein said resilient member extends from the arm.

20. A mechanism according to claim 19, wherein said resilient member is not integral with the arm.

21. A mechanism according to claim 20, wherein said resilient member is a U-shaped metal wire.

22. A mechanism according to claim 10, wherein said resilient member is able to move in a direction parallel to the axis of rotation of the arm.

23. A mechanism for articulation of a distal arm of a surgical instrument with respect to a proximal arm of the surgical instrument, said mechanism comprising:
    a pivot gear included on one of the arms and a pivot rack included on the other arm, wherein said pivot gear engages said pivot rack at a pivot; and
    an articulation rod pivotally attached to the distal arm for causing articulation of the distal arm with respect to the proximal arm about said pivot.

24. A mechanism according to claim 23, wherein said mechanism includes a backstop connected to the proximal arm and the distal arm.

25. A mechanism according to claim 24, wherein said backstop has a first end and a second end, wherein said first end is pivotally connected to one of the arms and said second end is slideably connected to a track in the other arm.

26. A mechanism according to claim 25, wherein said track has a curved portion which permits said backstop to move in accordance with the articulation angle.

27. A mechanism according to claim 24, wherein said backstop has a first end and a second end, wherein said first end is pivotally connected to the proximal arm.

28. A mechanism according to claim 27, wherein said second end is slideably connected to a track in the distal arm.

29. A mechanism according to claim 23, where one of the arms includes said pivot gear and the other arm includes said pivot rack.

30. A mechanism according to claim 23, wherein said pivot gear is positioned in an opening in the arm containing the pivot rack adjacent to the pivot rack.

31. A mechanism according to claim 23, wherein said pivot gear is connected to one of the arms and said pivot rack is connected to the other arm.

32. A mechanism according to claim 31, wherein said pivot rack is attached to an opening in the arm containing the pivot rack and said pivot gear is positioned in an opening in the same arm adjacent the pivot rack.

33. A mechanism according to claim 23, wherein said surgical instrument includes a flexible drive cable along said pivot.

34. A mechanism according to claim 23, wherein said mechanism comprises a pair of pivot gears and pivot racks.

35. A mechanism according to claim 34, wherein said pivot gears are connected to the distal arm and wherein said pivot racks are connected to the proximal arm.

36. A mechanism according to claim 35, wherein said mechanism includes a backstop connected to the proximal arm and the distal arm.

37. A mechanism according to claim 23, wherein the distal arm contains an actuation mechanism.

38. A mechanism according to claim 37, wherein said actuation mechanism is selected from the group consisting of a stapler mechanism, a clip applier mechanism, a scissors mechanism, a linear stapler mechanism, a GIA stapler mechanism, and a grasper mechansim.

39. A mechanism according to claim 23, wherein said articulation rod extends through the proximal arm.

40. A mechanism for transmitting force from a triggering mechanism to an actuation mechanism of a surgical device, the surgical device having an endoscopic arm, the endoscopic arm having a proximal arm and a distal arm connected at a joint, and a handle attached to the proximal arm, wherein the actuation mechanism is operatively connected to the distal arm and the triggering mechanism is operatively connected to the handle and the proximal arm, said mechanism comprising:
   a push drive cable having a proximal end and a distal end operatively connected at its proximal end to the triggering mechanism and operatively connected at its distal end to the actuation mechanism, wherein said drive cable is flexible; and
   a backstop supporting said drive cable and having a first end pivotally connected to one of the proximal and distal arms and a second end slidably connected to the other one of the proximal and distal arms.

41. A mechanism according to claim 40 wherein said drive cable includes an interior portion and a coating around said interior portion.

42. A mechanism according to claim 41, wherein said interior portion is a stainless steel portion.

43. A mechanism according to claim 41, wherein said coating is a plastic coating.

44. A mechanism according to claim 41, wherein said interior portion is a stainless steel portion and said coating is a plastic coating.

45. A mechanism according to claim 40 wherein said backstop moves in accordance with the articulation angle of the joint and supports said drive cable.

46. A mechanism according to claim 40 wherein said backstop supports said drive cable through the center of the pivot point of the joint.

47. A mechanism according to claim 40 wherein said backstop second end is slidably connected to a track in the other one of the proximal and distal arms.

48. A mechanism according to claim 47 wherein said track has a configuration which permits said backstop to move in accordance with the articulation angle of the joint.

49. A mechanism according to claim 48 wherein said backstop positions said drive cable through the center of the pivot point of the joint.

50. A mechanism according to claim 49 wherein said surgical device comprises:
   a pivot gear included on one of the proximal and distal arms and a pivot rack included on the other one of the proximal and distal arms, wherein said pivot gear engages said pivot rack at the joint; and
   an articulation rod pivotally attached to the distal arm for causing articulation of the distal arm with respect to the proximal arm about the joint.

51. A surgical instrument comprising:
   an endoscopic arm having a proximal end and a distal end;
   an actuation mechanism connected to said distal end of said endoscopic arm;
   a handle connected to said proximal end of said endoscopic arm, wherein said endoscopic arm is rotatably mounted to said handle;
   means for actuating said actuation mechanism; and
   means for adjustably maintaining an angle of rotation of said endoscopic arm with respect to said handle, said means comprising:
      a protrusion located between said handle and said endoscopic arm, said protrusion having a plurality of grooves;
      a U-shaped resilient metal wire member located between said endoscopic arm and said grooves, wherein said resilient member is rotatably adjustable between a plurality of fixed positions, wherein in each of said fixed positions said resilient member engages one of said grooves.

52. A surgical instrument comprising:
   an endoscopic arm having a proximal end and a distal end, wherein said proximal end and said distal end are connected at a joint;
   an actuation mechanism connected to said distal end of said endoscopic arm;
   a handle connected to said proximal end of said endoscopic arm;
   means for actuating said actuation mechanism; and
   means for articulation of said distal arm with respect to said proximal arm of said surgical instrument, said means comprising:
      a pivot gear on one of said distal and proximal arms and a pivot rack on the other of said distal and proximal arms, wherein said pivot gear engages said pivot rack at a pivot; and
      an articulation rod pivotally attached to said distal arm for causing articulation of said distal arm with respect to said proximal arm about said pivot.

53. A surgical instrument comprising:
   an endoscopic arm having a proximal arm and a distal arm, wherein said proximal arm and said distal arm are connected at a joint;
   an actuation mechanism operatively connected to said distal arm;
   a handle connected to said proximal end of said proximal arm; and means for actuating said actuation mechanism, wherein said means for actuating said actuation mechanism comprise:
- a triggering mechanism mounted on said handle for initiating the transmittal of said force from said proximal end of the proximal arm;
- a push drive cable having a proximal end and a distal end operatively connected at its proximal end to said triggering mechanism and operatively connected at its distal end to said actuation mechanism, wherein said drive cable is flexible; and
- a backstop supporting said drive cable and having a first end pivotally connected to one of said proximal and distal arms and a second end slidably connected to the other one of said proximal and distal arms.

54. A surgical instrument according to claim 53, wherein said triggering mechanism comprises a trigger pivotally mounted on the handle and a push rod attached to said trigger, said push rod engaging said drive cable.

55. A surgical instrument according to claim 53, wherein said triggering mechanism comprises:
- a trigger pivotally mounted on the handle;
- a first push rod attached to said trigger; and
- a second push rod attached to said first push rod, said second push rod engaging said drive cable.

56. A surgical instrument according to claim 53, wherein said triggering mechanism includes a pre-cock system.

57. A surgical instrument comprising:
- an endoscopic arm having a proximal arm and a distal arm, wherein said proximal arm and said distal arm are connected at a joint;
- an actuation mechanism operatively connected to said distal arm;
- a handle connected to the proximal end of said endoscopic arm, wherein said proximal arm is rotatably mounted to said handle;
- means for actuating said actuation mechanism; and
- means for adjustably maintaining an angle of rotation of said endoscopic arm with respect to said handle, said means comprising:
  - a protrusion located between said handle and said endoscopic arm, said protrusion having a plurality of grooves;
  - a resilient member located between said endoscopic arm and said grooves, wherein said resilient member is rotatably adjustable between a plurality of fixed positions, wherein in each of said fixed positions said resilient member engages one of said grooves;
- wherein said means for actuating said actuation mechanism comprise:
  - a triggering mechanism mounted on said handle for initiating the transmittal of said force from said proximal end of said proximal arm;
  - a push drive cable having a proximal end and a distal end operatively connected at its proximal end to said triggering mechanism and operatively connected at its distal end to said actuation mechanism, wherein said drive cable is flexible; and
  - a backstop supporting said drive cable and having a first end pivotally connected to one of said proximal and distal arms and a second end slidably connected to the other one of said proximal and distal arms.

58. A surgical instrument comprising:
- an endoscopic arm having a proximal arm and a distal arm, wherein said proximal arm and said distal arm are connected at a joint;
- an actuation mechanism operatively connected to said distal arm;
- a handle connected to the proximal end of said proximal arm;
- means for articulation of said distal arm with respect to said proximal arm of said surgical instrument;
- means for actuating said actuation mechanism; and
- means for adjustably maintaining an angle of rotation of said endoscopic arm with respect to said handle, said means comprising:
  - a protrusion located between said handle and said endoscopic arm, said protrusion having a plurality of grooves;
  - a resilient member located between said endoscopic arm and said grooves, wherein said resilient member is rotatably adjustable between a plurality of fixed positions, wherein in each of said fixed positions said resilient member engages one of said grooves;
- wherein said means for articulating said distal arm with respect to said proximal arm of said surgical instrument comprise
  - a pivot gear on one of said distal and proximal arms and a pivot rack on the other of said distal and proximal arms, wherein said pivot gear engages said pivot rack at a pivot; and
  - an articulation rod pivotally attached to said distal arm for causing articulation of said distal arm with respect to said proximal arm about said pivot.

59. A surgical instrument comprising:
- an endoscopic arm having a proximal arm and a distal arm, wherein said proximal arm and said distal arm are connected at a joint;
- an actuation mechanism connected to said distal arm;
- a handle connected to said proximal end of said proximal arm;
- means for articulation of said distal arm with respect to said proximal arm of said surgical instrument; and
- means for actuating said actuation mechanism, said means for actuating said actuation mechanism comprising
  - a triggering mechanism mounted on said handle for initiating the transmittal of said force from said proximal end of said proximal arm; and
  - a push drive cable having a proximal end and a distal end operatively connected at its proximal end to said triggering mechanism and operatively connected at its distal end to said actuation mechanism, wherein said drive cable is flexible;
- wherein said means for articulation of said distal arm with respect to said proximal arm of said surgical instrument comprise
  - a pivot gear on one of said distal and proximal arms and a pivot rack on the other of said distal and proximal arms, wherein said pivot gear engages said pivot rack at a pivot; and
  - an articulation rod pivotally attached to said distal arm for causing articulation of said distal arm with respect to said proximal arm about said pivot.

60. A surgical instrument comprising:
- an endoscopic arm having a proximal arm and a distal arm, wherein said proximal arm and said distal arm are connected at a joint;
- an actuation mechanism connected to said distal arm;
- a handle connected to said proximal end of said proximal arm, wherein said endoscopic arm is rotatably mounted to said handle;

means for adjustably maintaining an angle of rotation of said endoscopic arm with respect to said handle, said means comprising:
- a protrusion located between said handle and said endoscopic arm, said protrusion having a plurality of grooves;
- a resilient member located between said endoscopic arm and said grooves, wherein said resilient member is rotatably adjustable between a plurality of fixed positions, wherein in each of said fixed positions said resilient member engages one of said grooves;

means for articulation of said distal arm with respect to said proximal arm of said surgical instrument; said means for articulation comprising
- a pivot gear on one of said distal and proximal arms and a pivot rack on the other of said distal and proximal arms, wherein said pivot gear engages said pivot rack at a pivot; and
- an articulation rod pivotally attached to said distal arm for causing articulation of said distal arm with respect to said proximal arm about said pivot; and means for actuating said actuation mechanism, said means for actuating said actuation mechanism comprising
- a triggering mechanism mounted on said handle for initiating the transmittal of said force from said proximal end of said proximal arm; and
- a drive cable having a proximal end and a distal end operatively connected at its proximal end to said triggering mechanism and operatively connected at its distal end to said actuation mechanism, wherein said drive cable is flexible.

* * * * *